United States Patent [19]

Imaizumi

[11] 4,371,340
[45] Feb. 1, 1983

[54] DOWELL PIN AND METHOD OF MAKING DENTAL MODELS

[75] Inventor: Hiroo Imaizumi, Tokyo, Japan

[73] Assignee: Colpo Company, Ltd., Tokyo, Japan

[21] Appl. No.: 271,270

[22] Filed: Jun. 8, 1981

[30] Foreign Application Priority Data

Jun. 14, 1980 [JP] Japan ................... 55-83422[U]

[51] Int. Cl.³ ............................................ A61C 19/00
[52] U.S. Cl. ....................................... 433/74; 433/220
[58] Field of Search .................... 433/74, 53, 220, 221

[56] References Cited

U.S. PATENT DOCUMENTS

| | | | |
|---|---|---|---|
| 659,196 | 10/1900 | Johnson | 433/221 |
| 3,255,992 | 6/1966 | Kersten | 433/74 |
| 3,453,736 | 7/1969 | Waltke | 433/74 |
| 4,139,943 | 2/1979 | Dragan | 433/74 |
| 4,203,219 | 5/1980 | Wiener | 433/74 |
| 4,239,489 | 12/1980 | Ellman et al. | 433/220 |

FOREIGN PATENT DOCUMENTS 2115628 7/1973 Fed. Rep. of Germany ........ 433/74

Primary Examiner—Gene Mancene
Assistant Examiner—John J. Wilson
Attorney, Agent, or Firm—Browdy & Neimark

[57] ABSTRACT

A dowel pin is mainly made of the hard plastics and is substantially composed of a head to be implanted in the tooth model (primary plaster) and a pin body, a major portion of which is supported in the denture model (secondary plaster), and the pin body is frusto-concial, bar like or plate of moderate tapering, having one or both sides which are flat by grinding, and is provided with a passage at its center vertically running overall length from the head. A modefication has an auxiliary foot for checking rotation of the tooth model. Another modefication has wings on an upper portion of the pin body for concurrently removing the adjacent and plural teeth models from the denture model at once. Distinguishing of the head and the pin body is not essential.

10 Claims, 8 Drawing Figures

FIG_1 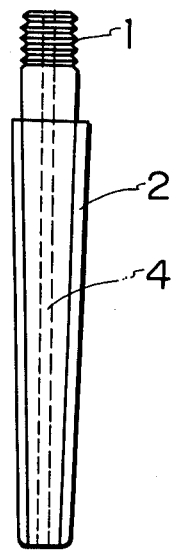 FIG_2 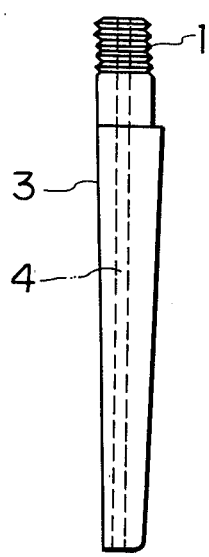 FIG_4 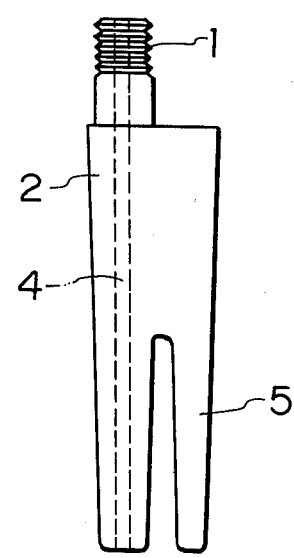
FIG_6 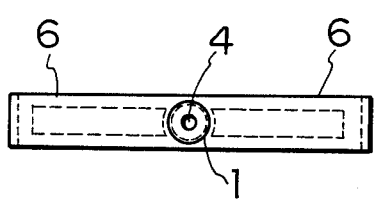 FIG_3 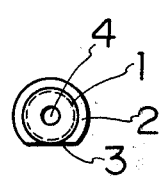
FIG_5 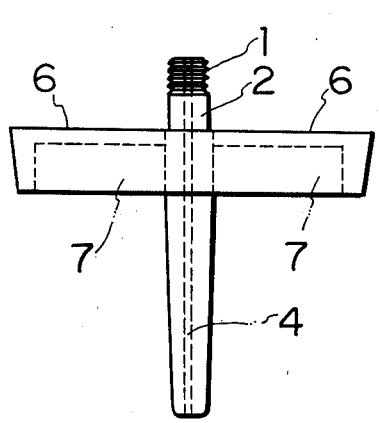 FIG_8 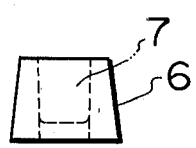
FIG_7 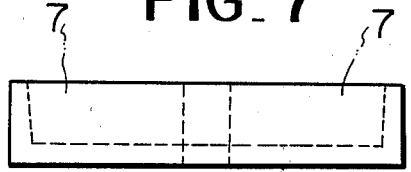

DOWELL PIN AND METHOD OF MAKING DENTAL MODELS

BACKGROUND OF THE INVENTION

1. Field of the Invention

This invention relates to a dental dowel pin to be used in making crowns or bridges. More particularly, the invention relates to a dowel pin which is used as a core for a tooth model to facilitate removing and attaching of the tooth model with respect to a denture model in order to improve the making of the crown or bridge. That is, a tooth model-detachable model or a divisional replacing model which have been adopted to the technical working model by the indirect treatment.

2. Description of the Prior Art

Conventional dowel pins are metallic, and are in general composed of a bar-like portion to be implanted in the tooth model (primary plaster) and a pin body a major portion of which is supported in the denture model (secondary plaster). The pin body is frusto-conical and has one or both sides which are flattened by grinding. There are some pins equipped with needles on their heads.

Those existing dowel pins have difficulties as mentioned hereafter and improvement thereon is needed, more specifically.

(a) For implanting the dowel pin into hardened plaster, the adhesive is poured into an inserting hole prepared in advance therein. This is followed by insertion of the pin, but then the adhesive often overflows, as there is no escape for the adhesive and air from the blind pin hole. When putting water on the overflow adhesive, it turns up and spoils the precision of the model.

(b) The dowel pin is often implanted before the primary plaster becomes hardened, and in this case not only is it difficult to insert the pin into the tooth model at its center portion but also the pin often falls down due to the greater specific gravity of the metallic pin compared to that of the plaster. Therefore, to avoid falling, a dowel pin equipped with a needle is made to stand directly into a tooth impression surface as the primary plaster is poured. After removing the impression surface, the needle projects from the surface of the hardened plaster, i.e., the surface of the tooth model, this projection has to be removed. However, it is very difficult to undertake this removal without hurting the surface of the tooth model. In addition, dowel pins with such needles are expensive. There are other ways of controlling the needle falling, but those are unsatisfactory as to ease of use and reliability.

(c) The prior art dowel pins are metallic. The part acting as a female model to the dowel pin is the plaster, and there is a big difference in hardness between the metal and the plaster. During many repetitions of removal and attachment of the tooth model, the plaster's inner surface at the inserting hole is effectively ground which reduces the precision of the model, so that the final placing relationship of the tooth model to the denture model is out of order. Thus, the crown or bridge fitting the teeth precisely does not result. Further, if the dowel pin were often cut or ground by error while trimming, the interior of the inserting hole of the secondary plaster would be injured by the burr caused by the expansibility of the metal. In addition, metallic pins are susceptible to rusting by contact with the plaster.

SUMMARY OF THE INVENTION

It is an object of the invention to provide a dowel pin which may be easily and exactly implanted in the tooth model at its center irrespectively of the repetition of implantation, or any other potentially disruptive working condition.

It is another object of the invention to provide a dowel pin which maintains the model precision without injuring the plaster even after many repetitions of attaching and removing the tooth model to and from the denture model and without causing any disorder of the attaching position of the tooth model in the denture model.

It is a further object of the invention to provide a dowel pin which does not cause the adhesive to overflow at the implantation site into the hardened plaster model nor injure the precision of the implant.

It is another object of the invention to provide a dowel pin which does not fall down if standing in unhardened.

It is a still further object of the invention to provide a dowel pin which may be removed from the denture model without deforming the continuous wax pattern.

Other and further objects, features and advantages of the invention will appear more fully from the following description.

BRIEF DESCRIPTION OF THE DRAWING

FIG. 1 is a front view showing one example of the invention,

FIG. 2 is a side view thereof,

FIG. 3 is a top plan view thereof,

FIG. 4 is a front view of another embodiment of the invention,

FIG. 5 is a front view of a further embodiment of the invention,

FIG. 6 is a plan view of the FIG. 5 embodiment,

FIG. 7 is a front view of a receptacle to be used integrally together with the embodiment shown in FIG. 5, and FIG. 8 is a side view of the FIG. 7 receptacle.

DETAILED DESCRIPTION OF THE INVENTION

The dowel pin according to the present invention is characterized by defining a passage therein at its center vertically running through its full length. The invention dowel pin can be of any shape such as frusto-conical, tubular, plate or other so long as it is removable, and it does not always have to be different as to the head and the pin body. Preferred embodiments will be described with reference to the attached drawing.

FIGS. 1 to 3 show one embodiment of the invention which would be most generally used. This is composed of a bar like head 1 to be implanted in the tooth model (primary plaster) and a pin body, a major portion of which is supported in the denture model (secondary plaster). The pin body 2 is moderate in tapering and has one or both sides 3 flattened as by grinding, and is provided with a passage or hole 4 at its center vertically running from the head 1 through the full length. The dowel pin is preferably made of hard plastics, especially those formed by mixing glass beads into polyacetal resin. By forming the passage 4 as mentioned above, when the dowel pin is implanted at its head into the hardened model of the primary plaster which holds an instantaneously hardenable adhesive therein, the excess adhesive and the air can escape via the hole 4 and not only flow outside the hole in the primary plaster.

FIG. 4 illustrates another embodiment of the dowel pin having an auxiliary foot 5 which is in general thinner than the pin body 2. The auxiliary foot serves to check rotation of the dowel pin and to exactly replace the tooth model having been once removed from the denture model. Using this embodiment, it is no longer necessary to form rotation checking grooves in the primary plaster on its reverse side, as is often done using conventional dowels.

FIGS. 5 to 8 depict a further embodiment. This dowel pin is furnished with wings 6, and it is used for concurrently removing adjacent plural teeth models all at once. For applying it to the hardened plaster, it is implanted at its head in the plaster and the wings 6 are attached to the plurality of teeth models on these bottoms, and the secondary plaster is poured. This pin is useful in such a case that the continuous wax pattern is removed from the denture model, and if the pin 2 is merely moved upwardly, the adjacent and plural teeth models may be removed all at once from the denture model. Thus, the wax pattern does not need partial and vertical fluctuation for removal and it is protected against deformation. When using it in not yet hardened and soft plaster, the wings 6 are modified with receptacles 7 and the pin is implanted such that part of the receptacle 7 is held in the primary plaster, and the secondary plaster is poured to hold the receptacle 7. This member 7 is then available in the hardened plaster. That is, using the receptacle 7, the dowel pin with the wings can be more smoothly removed.

The passage 4 characterizing this invention serves to avoid overflowing of the adhesive at the site of implantation of the dowel pin into the hardened plaster, and in addition it has other merits. A guide needle can be pierced into the tooth model at its center of the impression surface and this guide needle is passed into the hole 4, thereby enabling the dowel pin to stand. In this case, a part of the needle is a bit exposed at the bottom of the pin 2, and the primary plaster is poured, and after hardening the guide needle is drawn out from the bottom of the pin. Such a manner may exactly position the dowel pin centrally of the tooth model and eliminates the difficult work in the prior art of cutting the needle projecting on the surface of the tooth model without injuring the tooth model.

Further, the dowel pin according to the invention is in general made of hard plastics, especially polyacetal resin or the like, and has other merits than above mentioned. At first, being light in weight, it does not tend to if it is applied to non hardened plaster. The invention dowel pin is perfectly mirror-finished. Swirly lines are always left all over the surfaces of prior art metallic pins in their manufacturing steps. However, the present dowel pin has a smooth surface and no chance of rusting. The polyacetal resin is a crystalline high polymer excellent in mechanical strength with little friction and little abrasion and having as strong an elasticity as iron or steel. Owing to this low friction property the pin may be smoothly inserted and extracted, and it displays its merits especially when removing the pattern of one-piece bridges, or carrying out double implantations. Since it has elasticity to a certain extent, the pin can be inserted and extracted without breaking the model when the pins are not implanted perfectly in parallel.

Furthermore, when the denture model is set on the articulating machine and opened at jaws, and if the metallic dowel pin were then used on the tooth model of the upper jaw, the tooth model would drop owing to its own weight. However with the light weight hard plastic dowel pin of the invention, such dropping does not happen in spite of its low friction property.

While the invention has been described in detail above, it is to be understood that this detailed description is by way of example only, and the protection granted is to be limited only within the spirit of the invention and the scope of the following claims.

What is claimed is:

1. A dental dowel pin, said dowel pin being formed entirely of a relatively hard plastic material, said dowel pin being formed with a smooth mirror-like finish over substantially all of its external surface, said finish having relatively low friction and relatively low abrasion characteristics and said dowel pin being formed with a through passage running centrally through its entire length, whereby said dowel pin can be implanted in an already hardened dental model using adhesive in a prepared oversized opening in said model with the trapped air and excess adhesive caused by implantation of the pin escaping via said through passage to thus prevent adhesive from overflowing onto the outside of said pin and onto said mold.

2. A dowel pin as set forth in claim 1, and an auxiliary foot formed at the side of said dowel pin body.

3. A dowel pin as set forth in claim 1, and wings at the upper portion of said pin.

4. A dowel pin as set forth in claim 1, said relatively hard plastic material being polyacetal resin mixed with glass beads.

5. A dowel pin as set forth in claim 1, wherein the pin body tapers moderately and is flattened on one side longitudinally.

6. A method of making dental models having a dental dowel pin formed entirely of plastic and having a smooth mirror-like exterior surface and formed with a central through passage, comprising the steps of forming an opening in an already hardened denture model larger than the corresponding portion of said dowel pin to be received in said opening, inserting a suitable adhesive into said opening and standing said dowel pin into said adhesive in said opening; whereby said dowel pin due to its relatively light weight stands in said adhesive and in said opening without any additional support, and whereby all of the trapped air and any excessive adhesive escapes into said opening when said dowel pin is implanted in said adhesive in said opening rather than overflowing to the outside of said dowel pin onto said model.

7. The method of claim 6, wherein said plastic comprises a mixture of polyacetal resin and glass beads.

8. The method of claim 6, wherein the body of said pin is made to taper moderately over substantially its entire length, and a flat is formed on one longitudinal side of said pin.

9. The method of claim 6, and the step of providing wing means at the upper portion of said pin, and said wing means extending to the sides of said pin.

10. The method of claim 6, and the step of providing an extension in the form of a foot to one side of said pin.

* * * * *